(12) United States Patent
Wronska et al.

(10) Patent No.: US 9,512,493 B2
(45) Date of Patent: Dec. 6, 2016

(54) COMPOSITIONS, METHODS, AND KITS FOR NUCLEIC ACID HYBRIDIZATION

(75) Inventors: Danuta Wronska, Raleigh, NC (US); Katherine Schouest, Cary, NC (US)

(73) Assignee: Grifols Therapeutics Inc., Research Triangle Park, NC (US)

(*) Notice: Subject to any disclaimer, the term of this patent is extended or adjusted under 35 U.S.C. 154(b) by 292 days.

(21) Appl. No.: 14/237,746

(22) PCT Filed: Jul. 31, 2012

(86) PCT No.: PCT/US2012/048920
§ 371 (c)(1),
(2), (4) Date: Jun. 5, 2014

(87) PCT Pub. No.: WO2013/028316
PCT Pub. Date: Feb. 28, 2013

(65) Prior Publication Data
US 2014/0295408 A1    Oct. 2, 2014

Related U.S. Application Data

(60) Provisional application No. 61/526,773, filed on Aug. 24, 2011.

(51) Int. Cl.
*C07H 21/00* (2006.01)
*C12Q 1/68* (2006.01)
*C12Q 1/70* (2006.01)

(52) U.S. Cl.
CPC ............ *C12Q 1/703* (2013.01); *C12Q 1/6818* (2013.01); *C12Q 1/6832* (2013.01)

(58) Field of Classification Search
CPC .... C12Q 1/68; C12Q 1/6813; C12Q 1/6816; C12Q 1/6818; C07H 21/00
See application file for complete search history.

(56) References Cited

U.S. PATENT DOCUMENTS

| | | | | |
|---|---|---|---|---|
| 5,866,336 A * | 2/1999 | Nazarenko | ............ | C12Q 1/6818 435/6.12 |
| 5,871,921 A * | 2/1999 | Landegren | ............ | C12Q 1/6813 435/6.1 |
| 6,235,502 B1 * | 5/2001 | Weissman | ............ | C12Q 1/6827 435/6.1 |
| 7,482,443 B2 | 1/2009 | Shafer | | |
| 2003/0059811 A1 * | 3/2003 | Djaballah | ............ | G01N 33/542 435/6.11 |
| 2004/0072156 A1 * | 4/2004 | Nakamura | ............ | C12Q 1/6876 435/6.11 |
| 2006/0046265 A1 * | 3/2006 | Becker | ............ | C12P 19/34 435/5 |
| 2006/0088856 A1 | 4/2006 | Sorge et al. | | |
| 2006/0127940 A1 * | 6/2006 | Bao | ............ | C12Q 1/6818 435/6.11 |
| 2007/0231808 A1 * | 10/2007 | Gouda | ............ | C12Q 1/6818 435/6.12 |
| 2010/0173287 A1 | 7/2010 | Nakashima et al. | | |
| 2010/0203525 A1 | 8/2010 | Livak et al. | | |

FOREIGN PATENT DOCUMENTS

WO    WO 2011-028041 A2    3/2011

OTHER PUBLICATIONS

Cardullo et al.,Detection of nucleic acid hybridization by nonradiative fluorescence resonance energy transfer. PNAS 85 : 8790 (1988).*
Editorial : "Microbiology by numbers," Nature Reviews Microbiology 9 : 628 (Sep. 2011).*
Frankel et al., HIV-1: Fifteen Proteins and an RNA. Annual Reviews Biochemistry 67 : 1-25 (1998).*
Land et al., Insights from 20 years of bacterial genome sequencing. Funct Integr Genomics 15:141 (2015).*
Maldarelli, :We can now sequence a whole human genome in 26 hours. Popular Science (Sep. 2015).*
Patterson et al., Detection of HIV-1 DNA and messenger RNA in individual cells by PCR-driven in situ hybridization and flow cytometry. Science 260 :976 (1993).*
Schloss et al., Status of the Microbial Census. Microbiology and Molecular Biology Reviews 68 (4) : 686-691 (2004).*
Stratagene Catalog p. 39 (1988).*
International search report dated Feb. 18, 2013 in corresponding PCT Application No. PCT/US2012/048920 filed Jul. 31, 2012.

* cited by examiner

*Primary Examiner* — Ethan C Whisenant
(74) *Attorney, Agent, or Firm* — RatnerPrestia

(57) ABSTRACT

Polynucleotides having a first polynucleotide segment contiguous with a second polynucleotide segment that is downstream to the first, wherein the sequence of the first polynucleotide segment is complementary to the sequence of a first probe segment of a probe for detection of a target nucleic acid sequence, wherein the sequence of the second polynucleotide segment is complementary to the sequence of a second probe segment of the probe, wherein the second probe segment is downstream to the first probe segment, are provided. The polynucleotides may be employed with dual-labeled probes (DLPs) in assays for the detection of the target nucleic acid sequences.

2 Claims, 3 Drawing Sheets

```
                            TARGET
        3'-//-TGGTAGTTACTCCTTCGACGTCTTACCCTA-//-5'  (SEQ ID NO:3)
            | || || || || ||| || || ||| || || || |||
        FAM/ACCATCAATGAGGAAGCTGCAGAATGGGAT/BHQ-1   (SEQ ID NO:1)
            5'              PROBE              3'
```

```
        5'TCATTGATGGTATCCCATTCTG 3'  (SEQ ID NO:2)
              PROBE WRAPPER
```

FIG. 3

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Polynucleotide ("probe")

<400> SEQUENCE: 1
accatcaatg aggaagctgc agaatgggat                                30

<210> SEQ ID NO 2
<211> LENGTH: 22
<212> TYPE: DNA
<213> ORGANISM: Artificial Sequence
<220> FEATURE:
<223> OTHER INFORMATION: Polynucleotide ("probe wrapper")

<400> SEQUENCE: 2
tcattgatgg tatcccattc tg                                        22

<210> SEQ ID NO 3
<211> LENGTH: 30
<212> TYPE: DNA
<213> ORGANISM: Human immunodeficiency virus

<400> SEQUENCE: 3
atcccattct gcagcttcct cattgatggt                                30

COMPOSITIONS, METHODS, AND KITS FOR NUCLEIC ACID HYBRIDIZATION

CROSS REFERENCE TO RELATED APPLICATIONS

This application is a 371 application of International Application No. PCT/US2012/048920, filed Jul. 31, 2012, which claims priority to U.S. Provisional Patent Application 61/526,773, filed Aug. 24, 2011, all of which are incorporated by reference in its entirety herein.

FIELD OF THE INVENTION

The present invention relates to the field of methods and assays that involve nucleic acid hybridization.

BACKGROUND

Dual-labeled probes (DLPs) include polynucleotides labeled at one end with fluorescent dye (reporter) and on the opposite end with a quencher molecule. Such probes are often used in various hybridization assays including real-time PCR. In methods that employ DLP(s), when the quencher of the probe is physically close to the reporter, the fluorescence is quenched by physicochemical mechanisms of which FRET (Fluorescence Resonance Energy Transfer) is most common.

The quenching efficiency of a quencher can decrease rapidly with increasing distance between the reporter and the quencher. The distance between the quencher and the reporter molecules in a single free (unbound) intact DLP molecule can, in part, be dependent on the secondary structure of the DLP which is dependent upon the probe sequence. Those DLPs with more secondary structure may exist in a super-coiled conformation where the quencher and reporter are in close proximity and the quenching efficiency is high. Those DLPs with little or no secondary structure are predicted to exist in more relaxed conformation where the quencher and reporter are further apart and the quenching efficiency is lowered. DLPs with lower quenching efficiency can have high fluorescent background because some fluorescence of the reporter 'escapes' the effect of the quencher. High fluorescent background is undesirable in real-time PCR assays leading to, for example, low signal to noise ratio resulting in low assay sensitivity or signal drift whereby fluorescent signal from negative samples cross the threshold. When signal from an investigated sample crosses the threshold, a $C_T$ value is assigned to it. In automated data analysis where sample discrimination is based on $C_T$ values, negative samples displaying signal drift may be classified as positive causing unnecessary re-work.

One way of circumventing DLPs with high fluorescent background is to use attached universal duplex probes (AUDP), as reported in the literature, instead of DLPs. In AUDP, the reporter and quencher are attached respectively to the 5' and 3' ends of 2 different molecules of the probe complex which bind to each other. Thus the reporter and quencher are always in close proximity until the probe bearing the quencher is displaced and fluorescence is released. However because of their universal nature, the AUDP do not offer the additional specificity gate for PCR assays that DLPs provide.

There is a need to overcome the limitations, discussed above, of conventional hybridization probes and assays, in particular to provide compositions, methods, and kits that are effective for enhancing the performance of nucleic acid probes, in particular dual-labeled nucleic acid probes.

SUMMARY OF THE INVENTION

In one aspect, the present invention provides a polynucleotide having a first polynucleotide segment contiguous with a second polynucleotide segment that is downstream to the first, wherein the sequence of the first polynucleotide segment is complementary to the sequence of a first probe segment of a probe for detection of a target nucleic acid, wherein the sequence of the second polynucleotide segment is complementary to the sequence of a second probe segment of the probe, wherein the second probe segment is downstream to the first probe segment.

In another aspect, the present invention provides a composition comprising:

a) a polynucleotide having a first polynucleotide segment contiguous with a second polynucleotide segment that is downstream to the first; and b) a nucleic acid probe for detecting a target sequence, wherein the probe comprises a first probe segment and a second probe segment downstream to the first probe segment;

wherein the sequence of the first polynucleotide segment is complementary to the sequence of the first probe segment, wherein the sequence of the second polynucleotide segment is complementary to the sequence of the second probe segment.

In some aspects, the present invention provides a method for determining the presence of a target nucleic acid in a sample. The method comprises contacting the sample with a probe in the presence of a polynucleotide. The polynucleotide has a first polynucleotide segment contiguous with a second polynucleotide segment that is downstream to the first. The probe is a nucleic acid probe for detecting the target nucleic acid. The probe comprises a first probe segment and a second probe segment downstream to the first probe segment. The sequence of the first polynucleotide segment is complementary to the sequence of the first probe segment, wherein the sequence of the second polynucleotide segment is complementary to the sequence of the second probe segment.

In other aspects, the present invention provides a kit. The kit comprises a polynucleotide having a first polynucleotide segment contiguous with a second polynucleotide segment that is downstream to the first, wherein the sequence of the first polynucleotide segment is complementary to the sequence of a first probe segment of a probe for detection of a target nucleic acid, wherein the sequence of the second polynucleotide segment is complementary to the sequence of a second probe segment of the probe, wherein the second probe segment is downstream to the first probe segment.

BRIEF DESCRIPTION OF THE DRAWINGS

FIG. 3 is a schematic representation showing, in one embodiment, a probe wrapper and a probe, wherein the probe is hybridized to a target sequence.

DETAILED DESCRIPTION OF THE INVENTION

In one aspect, the present invention provides a polynucleotide (herein also referred to as a "probe wrapper") for hybridization to a nucleic acid probe used for the detection of target nucleic acid sequences. Generally, the probe wrapper hybridizes, under defined conditions, to both upstream and downstream regions of the nucleic acid probe.

Figure 1:
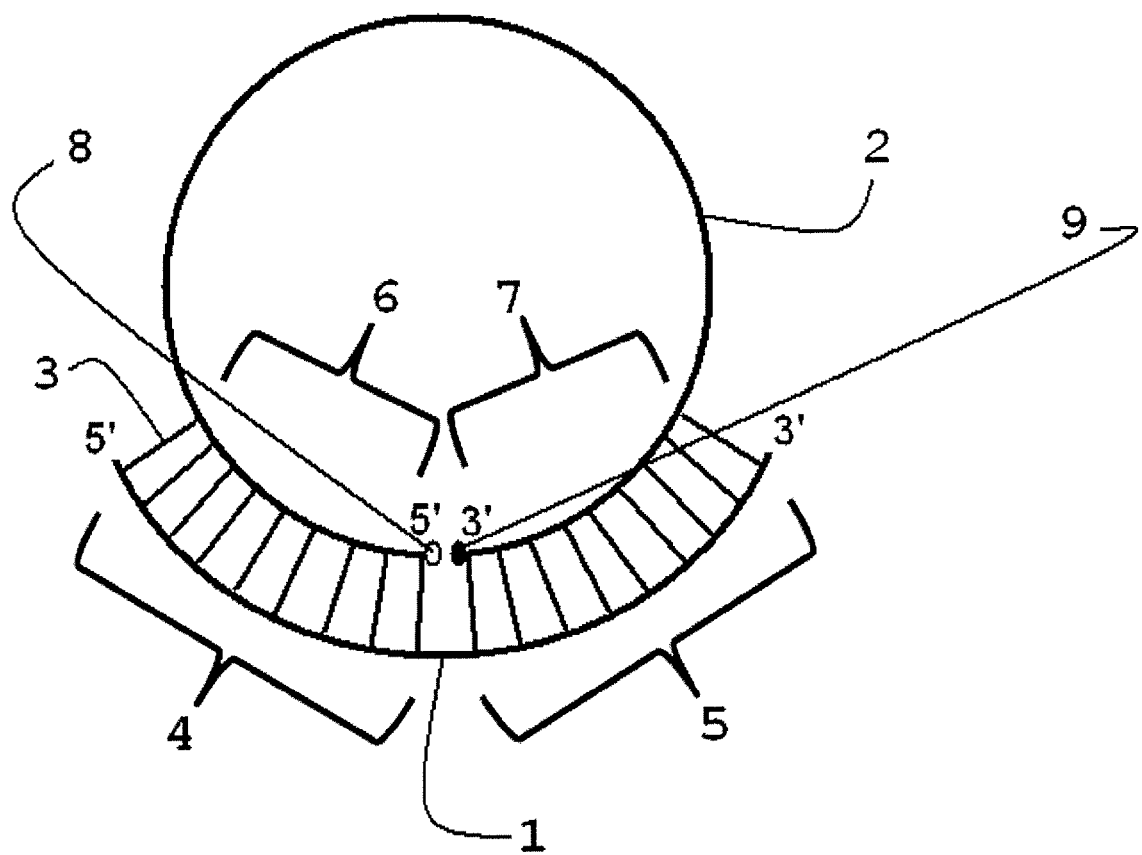
FIG. 1 is a schematic representation of one embodiment of a "probe wrapper" of the present invention hybridized to a probe.

FIG. 1 schematically illustrates one embodiment of the probe wrapper 1 hybridized to a DLP 2 by complementary base pairing 3. In the embodiment shown in FIG. 1, the probe wrapper is a single-stranded polynucleotide having a first polynucleotide segment 4 contiguous with a second polynucleotide segment 5 that is downstream to the first 4. The sequence of the first polynucleotide segment 4 is complementary to a first probe sequence that defines a first probe segment 6 of the probe 2 that further comprises a second probe segment 7 downstream to the first probe segment 6, the second probe segment 7 also comprising a nucleic acid sequence. The sequence of the second polynucleotide segment 5 of the probe wrapper 1 is complementary to the sequence of the second probe segment 7 of the probe 2. In FIG. 1, the probe 2 is depicted as further comprising a reporter 8 and a quencher 9 at its 5' and 3' ends, respectively.

Generally, the first probe segment, the second probe segment, or both are fully or sufficiently complementary to a target sequence to permit hybridization of the probe to the target in a sequence-specific manner.

Although, in some embodiments, the sequences of the first and the second polynucleotide segments of a probe wrapper are fully complementary to the sequences of the first and second probe segments of a probe, in other embodiments, hybridization of a probe wrapper with a probe is not limited to annealing of their respective segments by sequences that are fully complementary. In other words, the sequences of the annealing segments may not necessarily be fully complementary as long as the polynucleotide (i.e., the probe wrapper) specifically binds to the probe; may contain one or more universal bases, for example, inosine or 5-nitroindole; and may partially contain a base or a sequence which is not complementary.

In one embodiment, the sequence of the first polynucleotide segment of the probe wrapper is homologous to the reverse complement of the sequence of the first probe segment of the probe. In another embodiment, a percent homology between the sequence of the first polynucleotide segment and the reverse complement of the sequence of the first probe segment is at least about 90%, illustratively, about 90 to about 100%, and about 94 to about 96%. In some embodiments, the sequence of the first polynucleotide segment is the reverse complement of the sequence of the first probe segment.

In another embodiment, the sequence of the second polynucleotide segment of the probe wrapper is homologous to the reverse complement of the sequence of the second probe segment of the probe. In another embodiment, a percent homology between the sequence of the second polynucleotide segment and the reverse complement of the sequence of the second probe segment is at least about 90%, illustratively, about 90 to about 100%, and about 94 to about 96%. In some embodiments, the sequence of the second polynucleotide segment is the reverse complement of the sequence of the second probe segment.

In preferred embodiments, the probe wrapper is capable of hybridizing to a DLP having a reporter and a quencher.

For example, in some embodiments, the DLP is a single-stranded polynucleotide labeled at one end with a fluorescent dye (reporter) and on the opposite end with a quencher molecule. Without being held to any particular theory, it is believed that when the quencher is physically close to the reporter, the fluorescence is quenched by physicochemical mechanisms of which Fluorescence Resonance Energy Transfer (FRET) is most common. The probe wrapper of the present invention can hybridize, under defined conditions, to both upstream and downstream segments of the DLP thereby positioning the reporter and quencher in close proximity to each other (FIG. 1). This "wrapping" can increase the efficiency of fluorescence quenching by the quencher molecule, thus lowering the fluorescent background of free-form DLP (i.e., unconstrained or unengaged in target detection) during the detection step of a PCR cycle, for example. This results in elimination or significant reduction of signal drift which may cause a false positive result. Further, the interaction between the DLP and the probe wrapper is reversible—e.g., the molecules are separated during the denaturation step in a PCR cycle ensuring availability of the DLP for the next cycle of target detection.

In designing the probe wrapper, e.g. for use with a DLP with interactive labels (e.g., reporter/quencher), the upstream and downstream segments (i.e., the first and second polynucleotide segments, respectively) of the probe wrapper should be of sufficient length that under the conditions of an assay and at a detection temperature, when the DLP is not bound to a target, the probe wrapper and the probe are associated, and the label moieties of the probe are kept in close proximity to each other. Depending upon the assay conditions used, each of the first and second polynucleotide segments of the probe wrapper, independently, can be at least about 3 nucleotides in length, illustratively, about 3 to about 50 nucleotides, about 5 to 30 nucleotides, about 9 to about 20, and about 11 to about 15 nucleotides. In one embodiment, each segment, independently, is about 9 to about 11 nucleotides in length. Further, probe wrapper segments of larger lengths (e.g., greater than about 50 nucleotides) also can be employed depending on the assay conditions including the probe and/or target sequences. The actual length of each polynucleotide segment of a probe wrapper can be chosen with reference to the probe and/or target sequences such that the probe remains bound to the probe wrapper in the absence of target during a detection step.

Figure 2:
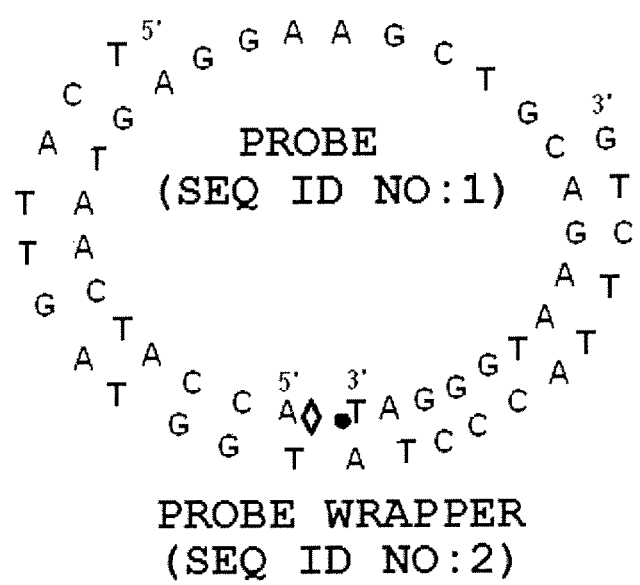
FIG. 2 is a schematic representation of some embodiments of the present invention: a probe having a sequence as set forth in SEQ ID NO:1 is depicted with a probe wrapper having a sequence as set forth in SEQ ID NO:2. Fluorophore ◇; Quencher ●.

For the probe wrapper/probe depicted in FIG. 2, the first and the second polynucleotide segments of the probe wrapper are shown as each having a length of 11 nucleotides that are fully complementary to the respective segments of the probe, which is a single-stranded polynucleotide having a total length of 30 nucleotides.

In some embodiments, the probe wrapper binds a DLP having a single pair of label moieties. In other embodiments, the DLP has more than one pair of label moieties. Further, there is no requirement for a one-to-one molecular correspondence between members of a label pair, especially where one member can affect, or be affected by, more than one molecule of the other member. Label moieties can interact so that at least one moiety can alter at least one physically measurable characteristic of another label moiety in a proximity-dependent manner. The characteristic signal of the label pair is detectably different depending on whether the probe is bound to the probe wrapper or to the target. In some embodiments, a label pair comprises one fluorescent moiety paired with two or more quenching moieties.

For example, referring to FIG. 1, the preferred label moieties are a single FRET pair, more preferably a fluorophore 8 and quencher 9. In that embodiment, the characteristic signal is fluorescence of a particular wavelength. When the probe is bound to the probe wrapper, the quencher moiety is capable of quenching fluorescence from the reporter moiety, wherein if the reporter moiety is stimulated by an appropriate frequency of light, a fluorescent signal is determined at a first level, which may be relatively low or about zero. When the probe is not bound to a probe wrapper, the quencher moiety is unable to quench fluorescence from the reporter moiety as efficiently as where the probe and probe wrapper are bound to each other, wherein if the reporter moiety is stimulated by an appropriate frequency of light, a fluorescent signal can be determined at a second level that, preferably, is greater than the first level. Further, if a target sequence is present, a signal at a third level can be determined, wherein the third level is greater than either the first or the second level.

In some embodiments, the probe wrapper, during assay conditions, reversibly binds sufficiently strongly to the probe under detection conditions in the absence of target sequence but sufficiently weakly that the hybridization of the probe and its target sequence, if present, is thermodynamically favored over the interaction of the probe wrapper with the probe.

In some embodiments, fluorescent dyes include, but are not limited to, FAM, BODIPY FL, Cy3™, Cy3.5™, Cy5™, Cy5.5™, EDANS, fluorescein, HEX, IAEDANS, JOE, Oregon Green™, (LC)Red640, (LC)Red705, ROX, TAMRA, TET, tetramethylrhodamine, Texas Red™ or combinations thereof.

In other embodiments, quencher dyes include, but are not limited to, BHQ-1™, BHQ-2™ BHQ-3™, DABCYL, metal clusters such as gold nanoparticles, and QSY7™

In one embodiment, the interactive labels include, but are not limited to, donor/acceptor pairs such as, for example, FAM/BHQ-1, fluorescein/tetramethylrhodamine, fluorescein/fluorescein, fluorescein/QSY7, fluorescein/LC RED640, fluorescein/LC Red705 IAEDANS/fluorescein, EDANS/DABCYL, BODIPY FL/BODIPY FL, TET/BHQ-1, JOE/BHQ-1, HEX/BHQ-1, Oregon Green/BHQ-1, TAMRA/BHQ-2, ROX/BHQ-2, Cy3/BHQ-2, Cy3.5/BHQ-2, Texas Red/BHQ-2, Texas Red/BHQ-2, Cy5/BHQ-3 and Cy5.5/BHQ-3.

Other useful label pairs include a reporter enzyme and appropriate inhibitor.

In another embodiment, the probe wrapper is capable of hybridizing to a DLP having a 5' and a 3' end labeled with a FAM and a BHQ1, respectively.

Although the second segment is contiguous with and immediately downstream of the first segment, as shown in FIG. 1, in other embodiments, the probe wrapper can further comprise a spacer between the first polynucleotide segment and the second polynucleotide segment.

The term "spacer" herein refers to a molecule that has a first end attached to the first polynucleotide segment and a second end attached to the second polynucleotide segment of the probe wrapper. Thus, the spacer molecule separates the first and the second segments, but is attached to both. The spacers may be synthesized directly or preferably attached as whole on the probe wrapper at specific locations. Bindings within the spacer may include, but is not limited to, carbon-carbon single bonds, carbon-carbon double bonds, carbon-nitrogen single bonds, or carbon-oxygen single bonds. Spacers suitable for use in the present invention include e.g. nucleotides, which contain adenine, cytosine, guanine and thymine as bases and deoxyribose as the structural element. Further, a nucleotide can, however, also comprise any artificial base known in the art, which is capable of base pairing using at least one of the aforesaid bases (for example inosine). Preferred spacers comprise also thymidine spacers, which may have a variable length. The spacer further may have suitable reactive groups, preferably at each end for the attachment to the first and second segments. Such reactive groups may comprise, for example, hydroxy-, thiol-, aldehyde-, amide- and thioamide-groups. In addition, the spacer may have side chains or other substitutions. The active group may be reacted by suitable methods known in the art, for example, preferably a covalent bond between the spacer and a segment of the probe wrapper to form a single contiguous probe wrapper molecule having the spacer between the first and the second probe wrapper segments.

In one embodiment, the probe wrapper has a 3'terminus that is modified to prevent polymerase extension by a polymerase. In another embodiment, the probe wrapper comprises a 3' terminus modified with a phosphate group, a phosphate ester, or an inverted 3'-3' linkage. Other methods and types of blocking are known to the skilled artisan and can be readily employed with the probe wrapper to prevent polymerase extension of its 3' end.

Non-limiting examples of probe wrappers and DLPs are provided in Table 1.

TABLE 1

Examples of sequences of DLPs and wrappers.

| Oligo-nucleotide function | Oligonucleotide sequence (5' to 3') |
|---|---|
| HIV Detection probe 1 | FAM/ACCATCAATGAGGAAGCTGCAGAATGGGAT/BHQ-1 (SEQ ID NO: 1) |
| HIV Probe wrapper 1 | TCATTGATGGTATCCCATTCTGphosphate (SEQ ID NO: 2) |

One of ordinary skill in the art will recognize that the behavior of nucleic acid molecules in complex solutions can not always be predicted with certainty, therefore, empirical testing is very useful in tailoring probe wrappers and/or probes according to the invention to perform optimally under particular assay conditions.

In other aspects, the present invention provides a composition comprising the probe wrapper and the probe.

In some embodiments, the composition comprises:

a) a probe wrapper, where the probe wrapper is a polynucleotide having a first polynucleotide segment contiguous with a second polynucleotide segment that is downstream to the first; and b) a nucleic acid probe for detecting a target sequence, wherein the probe comprises a first probe segment and a second probe segment downstream to the first probe segment;

wherein the sequence of the first polynucleotide segment is complementary to the sequence of the first probe segment, wherein the sequence of the second polynucleotide segment is complementary to the sequence of the second probe segment.

In one embodiment, the sequence of the first polynucleotide segment is the reverse complement of the sequence of the first probe segment. In another embodiment, the sequence of the second polynucleotide segment of the probe wrapper is homologous to the reverse complement of the sequence of the second probe segment of the probe.

In preferred embodiments, the probe nucleic acid strand, under a hybridization condition at a detection temperature, specifically, reversibly anneals to the probe wrapper nucleic acid strand in the absence of a target nucleic acid strand to form a probe/probe wrapper complex having a probe/probe wrapper $T_m$, wherein in the presence of the target nucleic acid strand, the probe nucleic acid strand preferentially anneals to the target nucleic acid strand to form a probe/target $T_m$.

Preferably, the probe/target $T_m$ is greater than the probe/probe wrapper $T_m$. In another embodiment, the probe/probe wrapper $T_m$, is greater than the detection temperature.

In some embodiments, wherein the probe comprises a signal-generating reporter (e.g., a fluorophore), a reporter signal at a first level may be determined when the probe is annealed to the probe wrapper. In other embodiments, the first level is less than a signal determined where a target sequence is present In one embodiment, the probe further comprises a reporter and a quencher.

Without being held to any particular theory, it is believed that separation of the probe/probe wrapper strand is driven by the thermodynamics of the formation of the probe/target helix. Formation of the probe/target helix can overcome the attraction of the probe/probe wrapper pair under assay conditions.

The nucleic acid molecules of the present invention including the probe wrappers and probes can be prepared from DNA, RNA, or combinations thereof. Further, in addition to single-stranded segments that participate in hybridization with probe sequences, in other embodiments, the nucleic acid molecules also may further comprise nucleic acid regions that are double-stranded. Further, the nucleic acid molecules may include modified nucleotides. Modified internucleotide linkages are useful in the nucleic acid molecules comprising deoxyribonucleotides and ribonucleotides to alter, for example, hybridization strength and resistance to non-specific degradation and nucleases. The links between nucleotides may include bonds other than phosphodiester bonds, for example, peptide bonds. Modified internucleotide linkages are well known in the art and include methylphosphonates, phosphorothioates, phosphorodithionates, phosphoroamidites and phosphate ester linkages. Dephospho-linkages are also known, as bridges, between nucleotides and include siloxane, carbonate, carboxymethyl ester, acetamidate, carbamate, and thioether bridges. "Plastic DNA," having for example N-vinyl, methacryloxyethyl, methacrylamide or ethyleneimine internucleotide linkages can also be used in nucleic acid molecules of the present invention. "Peptide Nucleic Acid" (PNA) is particularly useful because of its resistance to degradation by nucleases and because it forms a stronger hybrid with natural nucleic acids.

In still further aspects, the present invention provides a method for determining the presence of at least one target nucleic acid strand in a sample. The method comprises: contacting the sample with a probe in the presence of a probe wrapper.

In one embodiment, the probe wrapper is a polynucleotide having a first polynucleotide segment contiguous with a second polynucleotide segment that is downstream to the first; and the probe is a nucleic acid probe for detecting a target sequence, wherein the probe comprises a first probe segment and a second probe segment downstream to the first probe segment; wherein the sequence of the first polynucleotide segment is complementary to the sequence of the first probe segment, wherein the sequence of the second polynucleotide segment is complementary to the sequence of the second probe segment, wherein the probe further comprises a FRET pair comprising a fluorophore and a quencher.

In another embodiment, the first and the second probe segments, under a hybridization condition at a detection temperature, are capable of specifically and reversibly annealing, respectively, to the first and second polynucleotide segments of the probe wrapper in the absence of a target nucleic acid strand to form a probe/probe wrapper complex having a probe/probe wrapper $T_m$, wherein in the presence of the target nucleic acid strand, the probe is capable of preferentially annealing to the target nucleic acid strand to form a probe/target $T_m$.

In some embodiments, the method further comprises determining a change in a fluorescence signal of the probe at the detection temperature.

In other embodiments, a fluorescence signal at a first level is determined at the detection temperature when the probe is annealed to the probe wrapper, wherein the fluorescence signal at the detection temperature is greater than the first level where target nucleic acid strand is present in the sample.

In still further embodiments, assays in accordance with this invention can be multiplexed, i.e. more than one target nucleic acid analyte can be detected in one assay. Typically, in a multiplex assay, more than one specific nucleic acid probe that differ in the nature of their covalently attached dyes, is added to the mixture to be assayed. The dyes can be chosen to produce distinguishable fluorescent signals from each specific nucleic acid probe. The signals of the different dye combinations of the nucleic acid probes can be recorded simultaneously to detect and/or quantify the corresponding target nucleic acids at the same time.

In one embodiment, the method is a real time PCR. In another embodiment, the method is a multiplexed assay that includes multiple probe wrappers, probes, and/or targets in the same assay. In some embodiments, the method is a multiplexed, real time PCR including two or more different probes and their corresponding probe wrappers in accordance with the present invention.

In addition to homogenous assays, the nucleic acid molecules of the present invention can, in other embodiments, be employed in assays that are conducted on nucleic acid microarrays whereby the target nucleic acid analyte may be a mixture of nucleic acid sequences, consisting of up to hundreds of nucleic acid sequences, and in some instances of up to tens of thousands of nucleic acid sequences. This instance particularly applies to expression analysis, where many or all mRNA sequences that are present in a biological system, e.g. a certain cell type from a cell culture, are analyzed. Typically, the mRNA sequences can be amplified by reverse transcription PCR with universal primers prior to their use as analytes in the assay. In this setting all nucleic acid sequences present in the analyte are simultaneously applied to the microarray along with the appropriate probe wrapper(s), thus allowing the interaction of all nucleic acid sequences of the analyte with all nucleic acids that are present on the array. In other instances, the target nucleic acid analyte contains a limited number of up to a hundred nucleic acid sequences and in some instances only one nucleic acid sequence. Generally, in analysis on microarrays, the fluorescent signals generated are converted to sequence specific results through the known relation of the location of a spot on the array and the probe sequence attached to it.

Applications of the nucleic acid molecules of the present invention include the fields of in vitro diagnostics, including clinical diagnostics, research in the fields of molecular biology, high throughput drug screening, veterinary diagnostics, agricultural-genetics testing, environmental testing, food testing, industrial process monitoring, forensics, and insurance testing. In vitro diagnostics and clinical diagnostics are related to the analysis of nucleic acid samples drawn from the body to detect the existence of a pathogen (e.g., virus, bacteria), disease, or condition, its stage of development and/or severity, and the patient's response to treatment. In high throughput drug screening and development nucleic acids are used similarly to other agents, such as, antigens, antibodies, receptors, etc., to analyze the response of biological systems upon exposure to one or more compounds in a high sample number setting to identify drug leads. Veterinary diagnostics and agricultural genetics testing involve samples from a non-human animal or a plant species similar to in vitro diagnostics and to provide methods of quality control for agricultural genetic products and processes. In environmental testing, organisms and their toxins that indicate the pollution of an environmental medium, e.g., soil, water, air, etc., can be analyzed. Food testing includes the quantitation of organisms, e.g. bacteria, fungi, etc., as a method of quality control. In industrial process monitoring, nucleic acids are detected and/or quantified to indicate proper control of a production process and/or to generate a signal if such processes are out of control. In insurance testing, organisms and/or their toxins are identified in screening tests to determine the risk category of a client or to help approve candidates. One of ordinary skill in the art will recognize that probe wrappers and probes of the present invention can be employed for various other applications of the detection and/or quantitation of nucleic acids and new applications are being developed constantly.

In one embodiment, the nucleic acid molecules of the present invention including the probe wrappers and probes can be employed in assays for testing plasma donations and/or plasma manufacturing. For example, in some embodiments, assays include PCR testing of plasma donations and/or manufacturing for the presence or absence of infectious agents such as, but not limited to, HIV, HCV, parvovirus, bacteria, yeast, etc.

In some embodiments, RNA molecules (e.g., mRNA, viral genomic RNA) from a biological source (e.g., blood, semen, saliva, urine, spinal fluid, skin) are detected and/or quantified. Typically, the RNA molecules, if present, are converted to cDNA molecules and/or further amplified by PCR to provide the target nucleic acid analyte to be determined.

In other embodiments, assays are conducted with mRNA samples obtained from a biological system under different environmental conditions, such as exposures to varying concentration of a drug candidate or mixtures of drug candidates, which can provide data on the efficacy, the safety profile, the mechanism of action and other properties of the drug candidates that are required in drug development.

In some embodiments, the nucleic acid molecules of the present invention can be employed to detect or quantify DNA targets (e.g., viral genomic DNA, DNA polymorphisms) that may be present in a sample.

In still further aspects, the present invention provides a kit. For example, in some embodiments, assay kits of this invention include at least one probe wrapper designed for use with a probe. The probe wrapper can be a polynucleotide having a first polynucleotide segment contiguous with a second polynucleotide segment that is downstream to the first, wherein the sequence of the first polynucleotide segment is complementary to the sequence of a first probe segment of a probe, wherein the sequence of the second polynucleotide segment is complementary to the sequence of a second probe segment of the probe, wherein the second probe segment is downstream to the first probe segment.

Kits also may include the probe, instructions for performing the assay, and/or assay reagents, e.g., salts, buffers, nuclease inhibitors, restriction enzymes and denaturants. Kits also may include negative and positive controls. Further, amplification assay kits may include, in addition to some or all of the above, primers, nucleotides, and/or polymerases.

Components in the kit can either be obtained commercially or made according to well known methods in the art. In addition, the components of the kit can be in solution or lyophilized as appropriate. In one embodiment, the components are in the same compartment, and in another embodiment, the components are in separate compartments.

The following examples are provided for illustration only.

EXAMPLES

Example 1

Determining HIV

The presence of HIV RNA was determined in plasma samples using real-time PCR (RT-PCR) technology using standard protocols. Normal human plasma samples negative for HIV were used as negative controls.

HIV RNA extracted from plasma was subjected to one step reverse-transcriptase, real-time PCR amplification in the presence of a master mix comprising buffers, $Mg^{2+}$ ions, dNTPs, DMSO, MMLV reverse transcriptase, Taq polymerase, HIV specific primers, and probe 1, with or without probe wrapper 1. The reverse-transcriptase, real-time PCR reaction was performed using AB 7300 (Applied Biosystems, Foster City, Calif.) under thermal cycling conditions according to probe/probe wrapper melting temperatures. Following PCR amplification, the fluorescent signal generated was analyzed using the Sequence Detection System (SDS) software (Applied Biosystems, Foster City, Calif.) known in the art.

The results show detection of HIV in HIV positive plasma samples with $C_T$ values lower than 40. Negative controls had low fluorescent background remaining under the set threshold in the presence of probe wrapper. In the absence of probe wrapper, the fluorescent background in negative controls was high with some samples crossing the set threshold at $C_T$ value lower than 40 producing false positive results.

We claim:

1. The probe wrapper having the sequence of SEQ ID NO:2.

2. A kit comprising the probe wrapper of claim 1.

* * * * *